United States Patent [19]

Dektar et al.

[11] Patent Number: 4,980,492

[45] Date of Patent: Dec. 25, 1990

[54] SYNTHESIS OF TRIARYLSULFONIUM SALTS

[75] Inventors: John L. Dektar, San Jose; Nigel P. Hacker, Morgan Hill, both of Calif.

[73] Assignee: International Business Machines Corporation, Armonk, N.Y.

[21] Appl. No.: 317,235

[22] Filed: Feb. 28, 1989

Related U.S. Application Data

[63] Continuation-in-part of Ser. No. 152,729, Feb. 5, 1988, abandoned.

[51] Int. Cl.$^5$ .............................. C07F 9/06; C07F 9/92; C07F 9/68
[52] U.S. Cl. ................................................ 556/64; 568/77
[58] Field of Search ....................... 556/80, 64; 568/77

[56] References Cited

U.S. PATENT DOCUMENTS 4,161,478  7/1979  Crivello ............................ 556/80
4,544,646 10/1985  Pullukat et al. ................. 502/120

OTHER PUBLICATIONS

Wildi et al., *JACS*, 73 1965 (1951) pp. 1965–1967.

*Primary Examiner*—Gary P. Straub
*Assistant Examiner*—Stuart L. Hendrickson
*Attorney, Agent, or Firm*—Joseph G. Walsh; Robert B. Martin

[57] ABSTRACT

A triarylsulfonium salt is prepared in high yield and high purity by a two-step process involving a aryl Grignard reagent reacted with a diarylsulfoxide in a solvent which is a mixture of aliphatic and aromatic hydrocarbons, followed by a second step which is metathesis with $ZMF_6$, where Z is a metal or metal-like anion, and M is antimony, arsenic or phosphorus, preferably employing an ammonium salt and carried out in a non-aqueous solvent.

8 Claims, No Drawings

SYNTHESIS OF TRIARYLSULFONIUM SALTS

DESCRIPTION

The present application is a Continuation-in-Part of co-pending application Ser. No. 07/152,729 filed Feb. 5, 1988, now abandoned.

1. Technical Field

The present invention is concerned with an improved synthesis of triarylsulfonium salts.

2. Background Art

Triarylsulfonium salts are used as photo-acid initiators for polymerization and ester cleavage. They are also used as radical photoinitiators. They have, however, suffered from the disadvantage from being extremely expensive and also needing to be exceptionally pure when they are used.

The most commonly used synthesis of triarylsulfonium salts is that given by Crivello and Lam, *J. Polym. Sci.*, 17, 977 (1979). This method is usually called the "iodonium salt route". The method has the disadvantage of requiring the use of toxic iodonium salts. It has the additional disadvantage in that it is a two-step process and that expensive reagents are used in the lower yielding first step of the two-step process. The products from each step are impure, being isolated as colored oils. Multiple recrystallizations are required in order to obtain white crystalline products.

The literature also describes another method for the synthesis of triphenylsulfonium salts. This two-step process is described by the following equations:

STEP 1

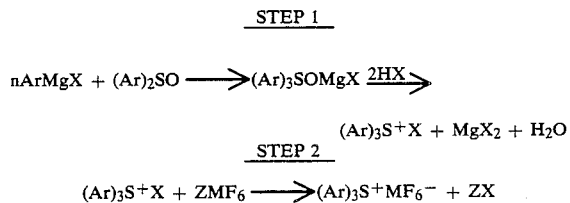

STEP 2

$(Ar)_3S^+X + ZMF_6 \longrightarrow (Ar)_3S^+MF_6^- + ZX$ wherein Ar is aromatic such as phenyl, tolyl, etc., X is a halogen such as bromide, and Z is a alkali metal such as sodium and M is antimony, arsenic or phosphorus. Step 1 of this synthesis is described in Wildi et al, *J. Amer. Chem. Soc.*, 73, 1965 (1951) and LaRochelle et al, *J. Amer. Chem Soc.*, 93, 6077 (1971). Step 2 of this synthesis is described by Smith, U.S. Pat. No. 4,173,476. It is with improvements in these synthetic methods that the present invention is concerned.

DISCLOSURE OF THE INVENTION

The above-described process is greatly improved by certain changes in the procedure. In the prior art, the Grignard reaction used either ether or ether-benzene co-solvents. According to the present invention, greatly higher yields are obtained using a solvent which is a mixture of liquid aromatic and aliphatic hydrocarbons. Using the solvent mixture of the present invention also has the advantages of shorter reaction times, 3 hours versus 18 hours in the prior art. Furthermore, less Grignard reagent can be used.

The present invention requires only 3 equivalents of Grignard reagent (Example 1) to give 60% yield of product, whereas the prior art requires 5 equivalents of the reagent and gives less product, 39% laRochelle et al, 49% Wildi et al. For direct comparison, when 2 equivalents of Grignard reagent are used, the present invention gives a 47% yield of product (Example 6), whereas the prior art, Wildi et al, reports only 14% yield of product. To demonstrate the necessity of the addition of aliphatic hydrocarbon co-solvent, the same reaction as Example 6 was run using 5 equivalents of Grignard reagent in benzene solvent and only 45% yield of product was obtained after 18 hours (Example 8). The aromatic co-solvent is not restricted to benzene; toluene (Example 7) can satisfactorily be used.

In the prior art, the second step of the reaction was carried out using aqueous solvents. This causes hydrolysis of the anion, giving undesirable side reactions and lower yields of product. We have now found that the procedure is greatly improved when a non-aqueous solvent is used. Examples 9-17 demonstrate the use of non-aqueous ketone, nitrile, alcohol and ester solvents.

Furthermore, we have found that the throughput for the process is improved when an ammonium salt is used for the metathetical second step of the process (Example 11). Using the improved process of the present invention, the products of each of the two steps of the reactions are white crystals. The process also has the additional advantage in that, in the process of the present invention, the expensive $MX_6$ anion is used in the high yielding second step.

The following Examples are given solely for the purposes of illustration and should not be thought as limitations on the present invention, many variations of which are possible without departing from the spirit or scope thereof.

GRIGNARD REACTIONS

Example 1

A 3.0 M solution of phenylmagnesium bromide in diethyl ether (50 ml, 0.15 mole) was distilled under vacuum with slow heating from 20° to 80° C. Benzene (40 ml) was added, followed by n-heptane (300 ml). The resulting mixture was stirred and a solution of diphenylsulfoxide 10.1 g, (0.050 mol), in benzene (60 ml) was added during 1 hour at 80° C. The mixture was stirred for 3 hours and cooled to room temperature. An 25% aqueous hydrobromic acid solution (180 ml) was slowly added to the reaction mixture (exotherm!). The layers were separated and the organic layer was extracted twice with 5% aqueous hydrobromic acid (2 x 30 ml). The combined aqueous extracts were extracted three times with dichloromethane (3×250 ml). The dichloromethane extracts were dried over magnesium sulfate, filtered and the organic solvent evaporated to leave triphenylsulfonium bromide (10.2 g, 60%), which was crystallized from dichloromethane/diethyl ether. M.p. 285-7° C.

Example 2

A 3.0 M solution of phenylmagnesium bromide in diethyl ether (50 ml, 0.15 mole) was distilled under vacuum with slow heating from 20° to 80° C. Benzene (40 ml) was added, followed by n-heptane (100 ml). The resulting mixture was stirred and a solution of diphenylsulfoxide 10.1 g, (0.050 mol), in benzene (60 ml) was added during 1 hour at 80° C. The mixture was stirred for 3 hours and cooled to room temperature. An 25% aqueous hydrobromic acid solution (180 ml) was slowly added to the reaction mixture (exotherm!). The layers were separated and the organic layer was extracted twice with 5% aqueous hydrobromic acid (2 x 30 ml). The combined aqueous extracts were extracted three times with dichloromethane (3 x 250 ml). The dichloromethane extracts were dried over magnesium sulfate, filtered and the organic solvent evaporated to leave triphenylsulfonium bromide (10.0 g, 59%).

Examples 3–5

Bromobenzene (28.4 g, 0.181 mol) was added to a stirred mixture of magnesium (4.3 g, 0.177 mol) in diethyl ether during hour. The resulting mixture of phenylmagnesium bromide and diethyl ether was distilled under vacuum with slow heating from 20° to 80° C. Benzene (50 ml) was added, followed by n-heptane (375 ml). The resulting mixture was stirred and a solution of diphenylsulfoxide 12.1 g, (0.0598 mol, in benzene (75 ml) was added during 1 hour at 80° C. The mixture was stirred for 3 hours and cooled to room temperature. An 25% aqueous hydrobromic acid solution (200 ml) was slowly added to the reaction mixture (exotherm!). The layers were separated and the organic layer was extracted twice with 5% aqueous hydrobromic acid (2 x 30 ml). The combined aqueous extracts were extracted three times with dichloromethane (3 x 250 ml). The dichloromethane extracts were dried over magnesium sulfate, filtered and the organic solvent evaporated to leave triphenylsulfonium bromide (12.3 g, 60%). Tris-(4-methylphenyl)sulfonium bromide and tris-(4-chlorophenyl)sulfonium bromide were prepared from their respective diarylsulfoxides and bromoarenes by the above procedure.

Example 6

A 3.0 M solution of phenylmagnesium bromide in diethyl ether (33 ml, 0.10 mole) was distilled under vacuum with slow heating from 20° to 80° C. Benzene (40 ml) was added, followed by n-heptane (100 ml). The resulting mixture was stirred and a solution of diphenylsulfoxide 10.1 g, (0.050 mol), in benzene (60 ml) was added during 1 hour at 80° C. The mixture was stirred for 18 hours and cooled to room temperature. An 25% aqueous hydrobromic acid solution (180 ml) was slowly added to the reaction mixture (exotherm!). The layers were separated and the organic layer was extracted twice with 5% aqueous hydrobromic acid (2 x 30 ml). The combined aqueous extracts were extracted three times with dichloromethane (3×250 ml). The dichloromethane extracts were dried over magnesium sulfate, filtered and the organic solvent evaporated to leave a residue which was crystallized from dichloromethane/diethyl ether to give triphenylsulfonium bromide (8.1 g, 47%).

Example 7

A 3.0 M solution of phenylmagnesium bromide in diethyl ether (42 ml, 0.126 mole) was distilled under vacuum with slow heating from 20° to 80° C. Toluene (40 ml) was added, followed by n-heptane (200 ml). The resulting mixture was stirred and a solution of diphenylsulfoxide 10.1 g, (0.050 mol), in benzene (60 ml) was added during 1 hour at 80° C. The mixture was stirred for 3 hours and cooled to room temperature. An 25% aqueous hydrobromic acid solution (180 ml) was slowly added to the reaction mixture (exotherm!). The layers were separated and the organic layer was extracted twice with 5% aqueous hydrobromic acid (2×30 ml). The combined aqueous extracts were extracted three times with dichloromethane (3×250 ml). The dichloromethane extracts were dried over magnesium sulfate, filtered and the organic solvent evaporated to leave a residue which was crystallized from dichloromethane/diethyl ether to give triphenylsulfonium bromide (7.7 g, 44%).

Example 8

A 3.0 M solution of phenylmagnesium bromide in diethyl ether (83 ml, 0.25 mole) was distilled under vacuum with slow heating from 20° to 80° C. Benzene (140 ml) was added, the resulting mixture was stirred and a solution of diphenylsulfoxide 10.1 g, (0.050 mol), in benzene (60 ml) was added during 1 hour at 80° C. The mixture was stirred for 18 hours and cooled to room temperature. An 25% aqueous hydrobromic acid solution (180 ml) was slowly added to the reaction mixture (exotherm!). The layers were separated and the organic layer was extracted twice with 5% aqueous hydrobromic acid (2×30 ml). The combined aqueous extracts were extracted three times with dichloromethane (3×250 ml). The dichloromethane extracts were dried over magnesium sulfate, filtered and the organic solvent evaporated to leave triphenylsulfonium bromide (7.7 g, 45%).

METATHESIS REACTIONS

Example 9

Triphenylsulfonium bromide (50 g, 0.146 mole) and sodium hexafluoroantimonate (38 g, 0.147 mole) were mixed in 300 ml of acetone and stirred for 3 hr. The suspension was filtered and the filtrate evaporated to yield a white solid (72.0 g, 100%). Recrystallization from ethanol gave white needles m.p. 203–5° C.

Example 10

Triphenylsulfonium bromide (15 g, 0.0437 mole) and sodium hexafluoroantimonate (11.3 g, 0.0437 mole) were mixed in 250 ml of acetone and stirred for 3 hr. The suspension was filtered and the filtrate evaporated to yield a white solid (21.8 g, 100%). Recrystallization from ethanol gave white needles.

Example 11

Triphenylsulfonium bromide (1.72 g, 5.01 mmole) and ammonium hexafluorophosphate (0.82 g, 5.03 mmole) were mixed in 60 ml of acetonitrile and stirred for 15 hr. The suspension was filtered and the filtrate evaporated to yield a white solid (2.02 g, 99%). Recrystallization from ethanol gave white needles m.p. 178–9° C.

Example 12

Triphenylsulfonium bromide (1.72 g, 5.01 mmole) and potassium hexafluorophosphate (1.38 g, 7.50 mmole) were mixed in 60 ml of acetone and stirred for 15 hr. The suspension was filtered and the filtrate evaporated to yield a white solid (2.01g, 98%). Recrystallization from ethanol gave white needles.

Example 13

Triphenylsulfonium bromide (2.00 g, 5.83 mmole) and sodium hexafluoroantimonate (1.50 g, 5.80 mmole) were mixed in 60 ml of acetone and stirred for 5 hr. The suspension was filtered and the filtrate evaporated to yield a white solid (2.87g, 99%).

Example 14

Triphenylsulfonium bromide (0.50 g, 1.46 mmole) and sodium hexafluoroantimonate (0.37 g, 1.43 mmole)

were mixed in 60 ml of ethylacetate and stirred for 5 hr. The suspension was filtered and the filtrate evaporated to yield a white solid (0.70g, 98%).

Example 15

Tris-(4-chlorophenyl)sulfonium bromide (0.85 g, 1.90 mmole) sodium hexafluoroantimonate (0.493 g, 1.91 mmole were mixed in 30 ml of acetone and stirred for 5 hr. The suspension was filtered and the filtrate evaporated to yield a white solid (1.13 g, 99%).

Example 16

Tris-(4-methylphenyl)sulfonium bromide (3.57 g, 9.26 mmole) and sodium hexafluoroantimonate (2.58 g, 9.97 mmole) were mixed in 60 ml of acetone and stirred for 5 hr. The suspension was filtered and the filtrate evaporated to yield a white solid (5.0g, 100%).

Example 17

Tris-(4-methylphenyl)sulfonium bromide (2.5 g, 6.49 mmole) and sodium hexafluoroantimonate (1.68 g, 6.49 mmole) were mixed in 60 ml of acetone and stirred for 5 hr. The suspension was filtered and the filtrate evaporated to yield a white solid (3.5g, 100%).

What is claimed is:

1. A process for the synthesis of a triarylsulfonium salt in which each of the aryl radicals are the same and are each selected from the group consisting of phenyl, methylphenyl halophenyl and unsubstituted hydrocarbon aryl, by the reaction of an aryl Grignard reagent with a diarylsulfoxide followed by a metathetical second reaction with a compound of the formula $ZMF_6$ where Z is selected from the group consisting of alkali metal and ammonium ions and M is selected from the group consisting of antimony, arsenic and phosphorus, wherein the improvement comprises carrying out the first step of the reaction in a solvent which is a mixture of liquid aromatic and aliphatic hydrocarbons.

2. A process as claimed in claim 1 wherein the improvement also comprises carrying out the metathetical second reaction in a solvent selected from the group consisting of ketone, nitrile, alcohol and ester solvents.

3. A process as claimed in claim 1 wherein the improvement also comprises using ammonium hexafluorophosphate in the metathetical reaction.

4. A process as claimed in claim 1 wherein the improvement also comprises using ammonium hexafluoroantimonate in the metathetical reaction.

5. A process as claimed in claim 2 where ethylacetate is the solvent in the metathetical reaction.

6. A process as claimed in claim 2 wherein acetone is the solvent in the metathetical reaction 7. A process as claimed in claim 2 wherein acetonitrile is the solvent in the metathetical reaction.

8. A process as claimed in claim 2 wherein ethanol is the solvent in the metathetical reaction.

* * * * *